(12) United States Patent
Cao et al.

(10) Patent No.: US 10,374,115 B2
(45) Date of Patent: Aug. 6, 2019

(54) MICROFLUIDIC SYSTEM AND METHOD FOR DRIVING THE SAME

(71) Applicant: BOE TECHNOLOGY GROUP CO., LTD., Beijing (CN)

(72) Inventors: Xueyou Cao, Beijing (CN); Xue Dong, Beijing (CN); Haisheng Wang, Beijing (CN); Xiaoliang Ding, Beijing (CN); Yingming Liu, Beijing (CN); Yanling Han, Beijing (CN); Yuzhen Guo, Beijing (CN); Pengpeng Wang, Beijing (CN); Chihjen Cheng, Beijing (CN); Ping Zhang, Beijing (CN); Wei Liu, Beijing (CN); Likai Deng, Beijing (CN); Yangbing Li, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/971,543

(22) Filed: May 4, 2018

(65) Prior Publication Data

US 2019/0097076 A1    Mar. 28, 2019

(30) Foreign Application Priority Data

Sep. 27, 2017   (CN) .......................... 2017 1 0891272

(51) Int. Cl.
 *H01L 27/14* (2006.01)
 *H01L 31/112* (2006.01)
 (Continued)

(52) U.S. Cl.
 CPC ........ *H01L 31/1126* (2013.01); *B01L 3/5027* (2013.01); *B01L 3/502715* (2013.01);
 (Continued)

(58) Field of Classification Search
 CPC ... H01L 31/1126; H01L 27/3227; B81B 1/00; B81B 2201/058; B01L 3/502715;
 (Continued)

(56) References Cited

U.S. PATENT DOCUMENTS 7,915,030 B2 * 3/2011 Inoue .................... B01L 3/0268
                                                          435/287.2
9,239,328 B2 * 1/2016 Chang .............. G01N 33/54366
 (Continued)

*Primary Examiner* — Shouxiang Hu
(74) *Attorney, Agent, or Firm* — Brooks Kushman P.C.

(57) ABSTRACT

A microfluidic system includes a liquid drop accommodation space, an array of photosensitivity detection circuits and an array of driving circuits between an upper substrate and a lower substrate. Each photosensitivity detection circuit includes a photosensitive transistor and a first gating transistor. The photosensitive transistor has a gate electrode coupled to a first scan signal line, a source electrode coupled to a first power supply voltage signal line, and a drain electrode coupled to a source electrode of the first gating transistor. The first gating transistor has a gate electrode coupled to a second scan signal line, and a drain electrode coupled to a read signal line. Each driving circuit includes a driving transistor and a driving electrode. The driving transistor has a gate electrode coupled to a third scan signal line, a source electrode coupled to a data signal line, and a drain electrode coupled to the driving electrode.

20 Claims, 7 Drawing Sheets

(51) Int. Cl.
*B81B 1/00* (2006.01)
*B01L 3/00* (2006.01)
*G01N 27/447* (2006.01)
*H01L 27/32* (2006.01)
*G09G 3/34* (2006.01)

(52) U.S. Cl.
CPC .......... *B01L 3/502792* (2013.01); *B81B 1/00* (2013.01); *G01N 27/44721* (2013.01); *H01L 27/3227* (2013.01); *B01L 2200/02* (2013.01); *B01L 2300/0645* (2013.01); *B01L 2400/0427* (2013.01); *B81B 2201/058* (2013.01); *G09G 3/344* (2013.01)

(58) Field of Classification Search
CPC ....... B01L 2400/0427; B01L 3/502792; B01L 2200/027; B01L 2300/0645; B01L 2400/0415; B01L 3/5027; B01L 2300/161; G01N 27/44721; G09G 3/344
See application file for complete search history.

(56) References Cited

U.S. PATENT DOCUMENTS

| | | | |
|---|---|---|---|
| 9,254,485 B2 * | 2/2016 | Chang | G01N 27/44791 |
| 2003/0164295 A1 * | 9/2003 | Sterling | B01L 3/50273 |
| | | | 204/450 |
| 2018/0369814 A1 * | 12/2018 | Walton | B01L 3/502715 |

* cited by examiner

MICROFLUIDIC SYSTEM AND METHOD FOR DRIVING THE SAME

CROSS-REFERENCE TO RELATED APPLICATION

This application claims priority to Chinese Patent Application No. 201710891272.9 filed on Sep. 27, 2017, which is incorporated herein by reference in its entirety.

TECHNICAL FIELD

The present disclosure relates to the field of micro-control technology, and in particular to a microfluidic system and a method for driving the same.

BACKGROUND

A microfluidic system is widely applied in many fields, particular in the field of chemistry and medicine. The microfluidic system in the related art usually detects a position and a size of a liquid drop by detecting impedance, and then uses a switch transistor to control a driving electrode, thereby controlling a movement trajectory of the liquid drop.

However, a separate device for detecting impedance is needed to be provided in the microfluidic system in the related art. Then the manufacturing process of the microfluidic system is complex. In addition, it is susceptible to signal interference when detecting impedance and then detection accuracy is adversely affected.

SUMMARY

One embodiment of the present disclosure provides a microfluidic system that includes: an upper substrate; a lower substrate that is opposite to the upper substrate; a liquid drop accommodation space between the upper substrate and the lower substrate; a first hydrophobic layer at an outermost surface of the upper substrate, and the outermost surface of the upper substrate facing the liquid drop accommodation space; a second hydrophobic layer at an outermost surface of the lower substrate, and the outermost surface of the lower substrate facing the liquid drop accommodation space; a common electrode layer between the upper substrate and the lower substrate; an array of photosensitivity detection circuits between the lower substrate and the second hydrophobic layer; and an array of driving circuits between the lower substrate and the second hydrophobic layer. Each photosensitivity detection circuit includes a photosensitive transistor and a first gating transistor. A gate electrode of the photosensitive transistor is coupled to a first scan signal line, a source electrode of the photosensitive transistor is coupled to a first power supply voltage signal line, and a drain electrode of the photosensitive transistor is coupled to a source electrode of the first gating transistor. A gate electrode of the first gating transistor is coupled to a second scan signal line, and a drain electrode of the first gating transistor is coupled to a read signal line. Each driving circuit includes a driving transistor and a driving electrode; a gate electrode of the driving transistor is coupled to a third scan signal line, a source electrode of the driving transistor is coupled to a data signal line, and a drain electrode of the driving transistor is coupled to the driving electrode.

Optionally, each photosensitivity detection circuit further includes a reset transistor and a follower transistor; and the reset transistor and the follower transistor are between the photosensitive transistor and the first gating transistor. A gate electrode of the reset transistor is coupled to a fourth scan signal line; a source electrode of the reset transistor is coupled to a reset signal line; a drain electrode of the reset transistor is coupled to the drain electrode of the photosensitive transistor and a gate electrode of the follower transistor, respectively. A source electrode of the follower transistor is coupled to a second power supply voltage signal line; a drain electrode of the follower transistor is coupled to the source electrode of the first gating transistor.

Optionally, each photosensitivity detection circuit further includes a second gating transistor between the photosensitive transistor and the reset transistor. A gate electrode of the second gating transistor is coupled to a fifth scan signal line; a source electrode of the second gating transistor is coupled to the drain electrode of the photosensitive transistor; and a drain electrode of the second gating transistor is coupled to the drain electrode of the reset transistor and the gate electrode of the follower transistor.

Optionally, the driving transistor and the first gating transistor are an identical transistor, and the second scan signal line and the third scan signal line are an identical signal line.

Optionally, each driving circuit further includes an amplifier transistor between the driving transistor and the data signal line. A gate electrode of the amplifier transistor is coupled to the data signal line and a constant voltage signal line, respectively; a source electrode of the amplifier transistor is coupled to a third power supply voltage signal line; and a drain electrode of the amplifier transistor is coupled to the source electrode of the driving transistor.

Optionally, the microfluidic system further includes a light shielding layer between the second hydrophobic layer and the photosensitivity detection circuits. Light transmission structures are formed in the light shielding layer at regions corresponding to some of the photosensitive transistors of the photosensitivity detection circuits.

Optionally, each light transmission structure is formed in the light shielding layer only at a region corresponding to one of every two adjacent photosensitive transistors.

Optionally, all transistors of the photosensitivity detection circuits and the driving circuits are bottom gate type transistors in an identical layer.

Optionally, the microfluidic system further includes a light shielding layer between the second hydrophobic layer and the photosensitivity detection circuits. The light shielding layer only covers two first gating transistors and one photosensitive transistor of every two adjacent photosensitivity detection circuits.

Optionally, the common electrode layer is between the upper substrate and the first hydrophobic layer.

Optionally, the microfluidic system further includes a plurality of integrators coupled to read signal lines in a one-to-one manner; a processor coupled with the integrators; and a driver coupled with the processor. The driver is coupled with the data signal lines.

One embodiment of the present disclosure further provides a method for driving the above microfluidic system, and the method includes: in an acquisition period, applying a turn-off signal to the first scan signal line, applying a turn-on signal to the second scan signal line, and acquiring a signal output from the read signal line; and in a driving period, applying a turn-on signal to the third scan signal line, and applying a driving signal to the data signal line.

Optionally, each photosensitivity detection circuit includes a reset transistor and a follower transistor, before the acquisition period, the method further includes: in a reset period, applying a turn-off signal to the first scan signal line, applying a turn-on signal to the fourth scan signal line, and applying a turn-on signal to the second scan signal line.

Optionally, each photosensitivity detection circuit further includes a second gating transistor, the method further includes: applying a turn-on signal to the fifth scan signal line in the reset period and in the acquisition period.

Optionally, in the reset period, a duration for applying the turn-on signal to the fifth scan signal line is less than a duration for applying the turn-on signal to each of the fourth scan signal line and the second scan signal line. In the acquisition period, a duration for applying the turn-on signal to the fifth scan signal line is less than a duration for applying the turn-on signal to the second scan signal line.

Optionally, in the acquisition period, the turn-on signal is continuously applied to the second scan signal line.

Optionally, in the acquisition period, two turn-on signals with a time interval are applied to the second scan signal line.

One embodiment of the present disclosure further provides a microfluidic system that includes: an upper substrate; a lower substrate that is opposite to the upper substrate; a liquid drop accommodation space between the upper substrate and the lower substrate; a first hydrophobic layer at an outermost surface of the upper substrate, and the outermost surface of the upper substrate facing the liquid drop accommodation space; a second hydrophobic layer at an outermost surface of the lower substrate, and the outermost surface of the lower substrate facing the liquid drop accommodation space; a common electrode layer between the upper substrate and the lower substrate; an array of first photosensitivity detection circuits between the lower substrate and the second hydrophobic layer; an array of second photosensitivity detection circuits between the lower substrate and the second hydrophobic layer; and an array of driving circuits between the lower substrate and the second hydrophobic layer. Each of the first photosensitivity detection circuits and second photosensitivity detection circuits includes a photosensitive transistor and a first gating transistor. A gate electrode of the photosensitive transistor is coupled to a first scan signal line, a source electrode of the photosensitive transistor is coupled to a first power supply voltage signal line, and a drain electrode of the photosensitive transistor is coupled to a source electrode of the first gating transistor. A gate electrode of the first gating transistor is coupled to a second scan signal line, and a drain electrode of the first gating transistor is coupled to a read signal line. Each driving circuit includes a driving transistor and a driving electrode; a gate electrode of the driving transistor is coupled to a third scan signal line, a source electrode of the driving transistor is coupled to a data signal line, and a drain electrode of the driving transistor is coupled to the driving electrode. The photosensitive transistor of each of the first photosensitivity detection circuits is configured to perform optical detection; and the photosensitive transistor of each of the second photosensitivity detection circuits is configured to be used as a comparison transistor.

Optionally, the first photosensitivity detection circuits and the second photosensitivity detection circuits are alternately arranged.

Optionally, the microfluidic system further includes a light shielding layer between the second hydrophobic layer and the first and second photosensitivity detection circuits. The light shielding layer only covers the second photosensitivity detection circuits.

BRIEF DESCRIPTION OF THE DRAWINGS

The accompanying drawings, which are incorporated in and constitute a part of this specification, illustrate embodiments consistent with the present disclosure and, together with the description, serve to explain the principles of the present disclosure.

FIG. 2b is a diagram of time sequences of signals for the circuit shown in FIG. 2a;

FIG. 3b is a diagram of time sequences of signals for the circuit shown in FIG. 3a;

FIG. 4b is a diagram of time sequences of signals for the circuit shown in FIG. 4a;

FIG. 4c is another diagram of time sequences of signals for the circuit shown in FIG. 4a;

FIG. 5b is a diagram of time sequences of signals for the circuit shown in FIG. 5a.

DETAILED DESCRIPTION

Figure 1A:
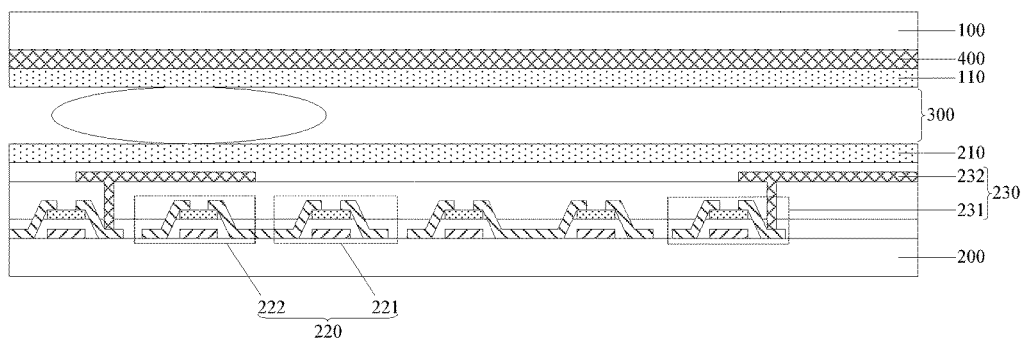
FIG. 1a is a schematic view of a microfluidic system according to an embodiment of the present disclosure.

Reference will now be made in detail to exemplary embodiments, examples of which are illustrated in the accompanying drawings. The following description refers to the accompanying drawings in which the same numbers in different drawings represent the same or similar elements unless otherwise indicated. The implementations set forth in the following description of exemplary embodiments do not represent all implementations consistent with the disclosure. Instead, they are merely examples of devices and methods consistent with aspects related to the disclosure as recited in the appended claims.

Referring to FIG. 1, one embodiment of the present disclosure provides a microfluidic system, and the microfluidic system includes an upper substrate 100, a lower substrate 200, a liquid drop accommodation space 300, a first hydrophobic layer 110, a second hydrophobic layer 210, a common electrode layer 400, a plurality of photosensitivity detection circuits 220 and a plurality of driving circuits 230. The upper substrate 100 is opposite to the lower substrate 200. The liquid drop accommodation space 300 is defined between the upper substrate 100 and the lower substrate 200. The first hydrophobic layer 110 is at an outermost surface of the upper substrate 100, and the outermost surface of the upper substrate 100 faces the liquid drop accommodation space 300. The second hydrophobic layer 210 is at an outermost surface of the lower substrate 200 and the outermost surface of the lower substrate 200 faces the liquid drop accommodation space 300. The common electrode layer 400 is between the upper substrate 100 and the lower substrate 200. The photosensitivity detection circuits 220 are between the lower substrate 200 and the second hydrophobic layer 210, and are arranged in an array. The driving circuits 230 are between the lower substrate 200 and the second hydrophobic layer 210, and are arranged in an array.

Figure 2A:
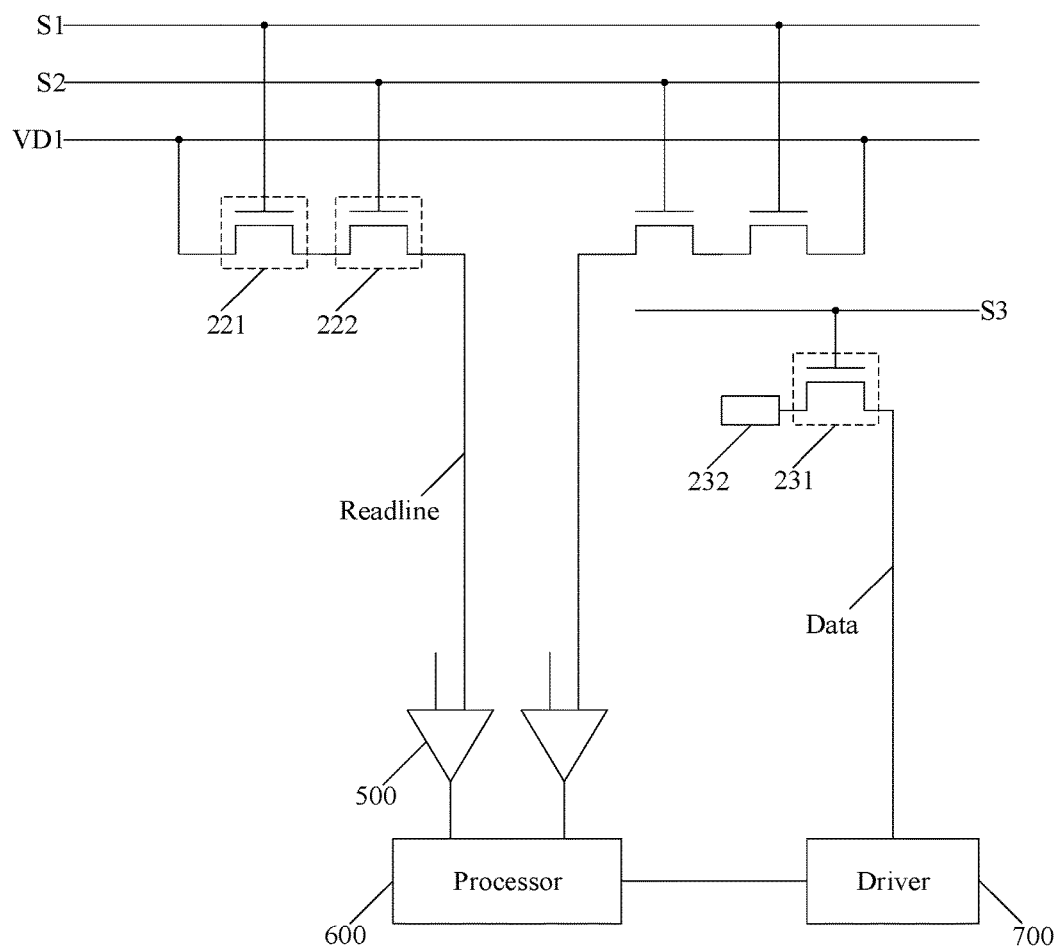
FIG. 2a is a first schematic diagram of a circuit of the microfluidic system according to an embodiment of the present disclosure.

In one embodiment, as shown in FIG. 1a, each photosensitivity detection circuit 220 includes a photosensitive transistor 221 and a first gating transistor 222. As shown in FIG. 2a, a gate electrode of the photosensitive transistor 221 is coupled to a first scan signal line S1, a source electrode of the photosensitive transistor 221 is coupled to a first power supply voltage signal line VD1, and a drain electrode of the photosensitive transistor 221 is coupled to a source electrode of the first gating transistor 222. A gate electrode of the first gating transistor 222 is coupled to a second scan signal line S2, and a drain electrode of the first gating transistor 222 is coupled to a read signal line Readline.

In one embodiment, as shown in FIG. 1a, each driving circuit 230 includes a driving transistor 231 and a driving electrode 232. As shown in FIG. 2a, a gate electrode of the driving transistor 231 is coupled to a third scan signal line S3, a source electrode of the driving transistor 231 is coupled to a data signal line Data, and a drain electrode of the driving transistor 231 is coupled to the driving electrode 232.

Specifically, in the above microfluidic system of one embodiment of the present disclosure, based on the photosensitive characteristics of the photosensitive transistor 221, a position and a size of one liquid drop can be detected by analyzing differences between a photosensitive signal received by the photosensitive transistor 221 that is covered by the liquid drop and a photosensitive signal received by the photosensitive transistor 221 that is not covered by any liquid drop. Then, a movement trajectory of the liquid drop can be controlled by using the driving transistor 231 to control the driving electrode 232. Since both of the photosensitivity detection circuit 220 and the driving circuit 230 implement their functions through transistors without additional detection components, the manufacturing process is simplified and then the manufacturing efficiency can be improved.

Specifically, a working principle of the above microfluidic system is described hereinafter.

Figure 2B:
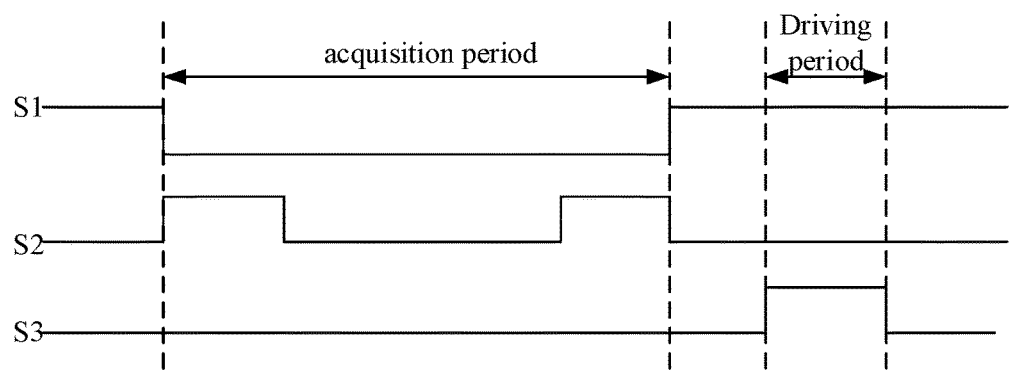

As shown in FIG. 2b, in an acquisition period, a turn-off signal may be applied to the first scan signal line S1 to enable the photosensitive transistor 221 to be turned off so that the photosensitive transistor 221 can work in the best state of photosensitivity. The photosensitive transistor 221 that is turned off can generate a photocurrent in response to light irradiation. When light passes through one liquid drop and then is irradiated to some photosensitive transistors 221, these photosensitive transistors 221 can generate a photocurrent. There is a signal difference between the photocurrent generated by one photosensitive transistor 221 that is covered by one liquid drop when light passes through the one liquid drop and then is irradiated to the one photosensitive transistor 221 that is covered by one liquid drop, and a photocurrent generated by one photosensitive transistor 221 that is not covered by any liquid drop when light is directly irradiated to the one photosensitive transistor 221 that is not covered by any liquid drop. In the acquisition period, a turn-on signal may be simultaneously applied to the second scan signal line S2 to enable the first gating transistor 222 to be turned on. Then, photocurrents generated by the photosensitive transistors 221 can be output through the read signal lines Readline, and a position and a size of the liquid drop can be determined by detecting the signal difference between the photocurrents. Since the above detection is carried out based on the photosensitive characteristics of the photosensitive transistors, signal interference can be avoided, thereby improving detection accuracy.

Then, it is determined which driving circuit 230 is to be controlled by comparing the determined position and size of the liquid drop with a movement trajectory set for the liquid drop. For the driving circuit 230 to be controlled, as shown in FIG. 2b, in a driving period, a turn-on signal is applied to the third scan signal line S3 to enable the driving transistor 231 to transmit a driving signal from the data signal line Data to the driving electrode 230. At this point, a potential difference generated between the driving electrode 230 and the common electrode 400 affects shrink angle of the liquid drop, thereby changing surface tension of the liquid drop and then enabling the liquid drop to move. As a result, the movement trajectory of the liquid drop can be controlled.

Optionally, in the above microfluidic system, in order to implement optical detection with the photosensitivity detection circuit 220, a passive light source such as ambient light or an additional active light source may be adopted.

Optionally, in the above microfluidic system, in order to ensure that the photosensitive transistor 221 can receive light of sufficient intensity, films above the photosensitive transistor 221 may be made of transparent materials as much as possible. For example, the common electrode layer 400 and the driving electrode 232 may be made of transparent indium oxide material; the first hydrophobic layer 110, the second hydrophobic layer 210 and the upper substrate 100 may be made of light transmitting material, so that light can pass through the films above the photosensitive transistor 221 and then reach the photosensitive transistor 221. In response to the light irradiated to the photosensitive transistor 221, the photosensitive transistor 221 generates a photocurrent, thereby realizing photoelectric conversion and then achieving the purpose of acquiring signals.

Optionally, in the above microfluidic system, in order to enable the photosensitive transistor 221 to have good photosensitivity, an active layer of the photosensitive transistor 221 may be made of amorphous silicon.

Figure 1B:
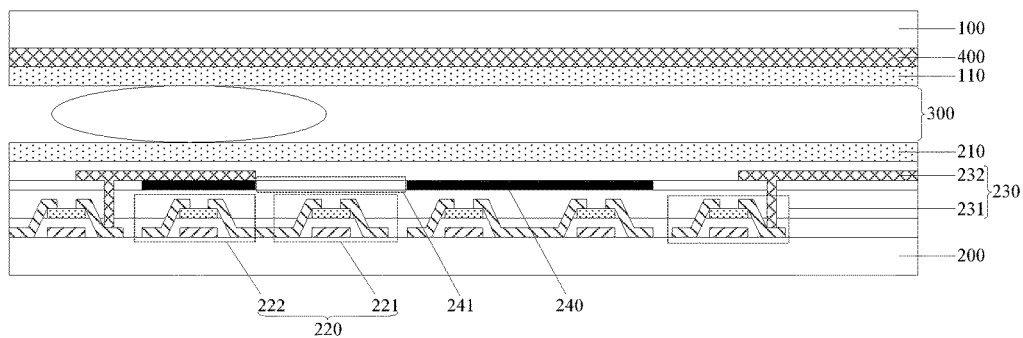
FIG. 1b is another schematic view of a microfluidic system according to an embodiment of the present disclosure.

Optionally, in the above microfluidic system, as shown in FIG. 1b, the above microfluidic system may further include a light shielding layer 240 between the second hydrophobic layer 210 and the photosensitivity detection circuits 220. Light transmission structures are formed in the light shielding layer 240 at regions corresponding to some photosensitive transistors 221.

Specifically, the light transmission structures 241 may be formed in the light shielding layer 240 at regions corresponding to a part of the photosensitive transistors 221, and this part of the photosensitive transistors 221 can be used to implement normal optical detection. The light shielding layer 240 may shield the rest part of the photosensitive transistors 221, and the rest part of the photosensitive transistors 221 can be used as comparison transistors for de-noising. The light shielding layer 240 can ensure that light irradiation does not affect characteristics of the photosensitive transistor 221 that are not used for optical detection. Further, the light shielding layer 240 can shield the first gating transistor 222 from light irradiation, thereby preventing the first gating transistor 222 from being affected by the light irradiation.

Optionally, in the above microfluidic system, one light transmission structure 241 is formed in the light shielding layer 240 only at a region corresponding to one of every two adjacent photosensitive transistors 221.

Specifically, every two adjacent photosensitivity detection circuit 220 may be taken as one group. In one group, one photosensitivity detection circuit 220 is used for optical detection, and may be referred as a first photosensitivity detection circuit; and the other photosensitivity detection circuit 220 is taken as a comparison, and may be referred as a second photosensitivity detection circuit. In FIG. 1a and FIG. 1b, the left photosensitivity detection circuit 220 is used for optical detection, and the right photosensitivity detection circuit 220 is taken as a comparison. Of course, in the above microfluidic system, the comparison transistor may be arranged in other manners.

Optionally, in the above microfluidic system, as shown in FIG. 1a and FIG. 1b, all the transistors of the photosensitivity detection circuits 220 and the driving circuits 230 may be bottom gate type transistors arranged in an identical layer.

Specifically, all the transistors of the photosensitivity detection circuits 220 and the driving circuits 230 arranged in an identical layer means that gate electrodes of all the transistors are made from an identical film layer, active layers of all the transistors are made from an identical film layer and source-drain electrodes of all the transistors are made from an identical film layer. In this way, the manufacturing process can be simplified and improve manufacturing efficiency.

Optionally, in the above microfluidic system, as shown in FIG. 1a and FIG. 1b, the common electrode layer 400 is between the upper substrate 100 and the first hydrophobic layer 110. Of course, the common electrode layer 400 may be between the lower substrate 200 and the second hydrophobic layer 210.

Optionally, in the above microfluidic system, as shown in FIG. 2a, FIG. 3a, FIG. 4a and FIG. 5a, the microfluidic system may further include a plurality of integrators 500, a processor 600 and a driver 700. The integrators 500 are coupled to the read signal lines Readline in a one-to-one manner. The processor 600 is coupled with the integrators 500. The driver 700 is coupled with the processor 600. The driver 700 is coupled with the data signal lines Data.

Specifically, the integrator 500 can read a photocurrent signal output from the read signal line Readline, integrate and convert the photocurrent signal into a corresponding voltage signal. Then, the processor 600 performs a digital-analog conversion to the voltage signal to determine a position and a size of the liquid drop, determines a driving signal and which driving circuit 230 to be controlled by comparing the determined position and size of the liquid drop with a movement trajectory set for the liquid drop. After the driver 700 receives the driving signal and improves the driving ability of the driving signal, the driver 700 transmits the driving signal to the driving transistor 231 through the data signal line Data, thereby controlling movement of the liquid drop.

Optionally, in the above microfluidic system, the processor 600 may implement a field-programmable gate array (FPGA) and an integrated circuit (IC) to achieve its function. The integrated circuit is used to collect voltage signals output from the integrators 500 that are coupled to the read signal lines Readline. The field-programmable gate array is used to process signals, etc. In addition, a computer may be coupled to the field-programmable gate array and shows in real time the position and size of the liquid drop.

Figure 3A:
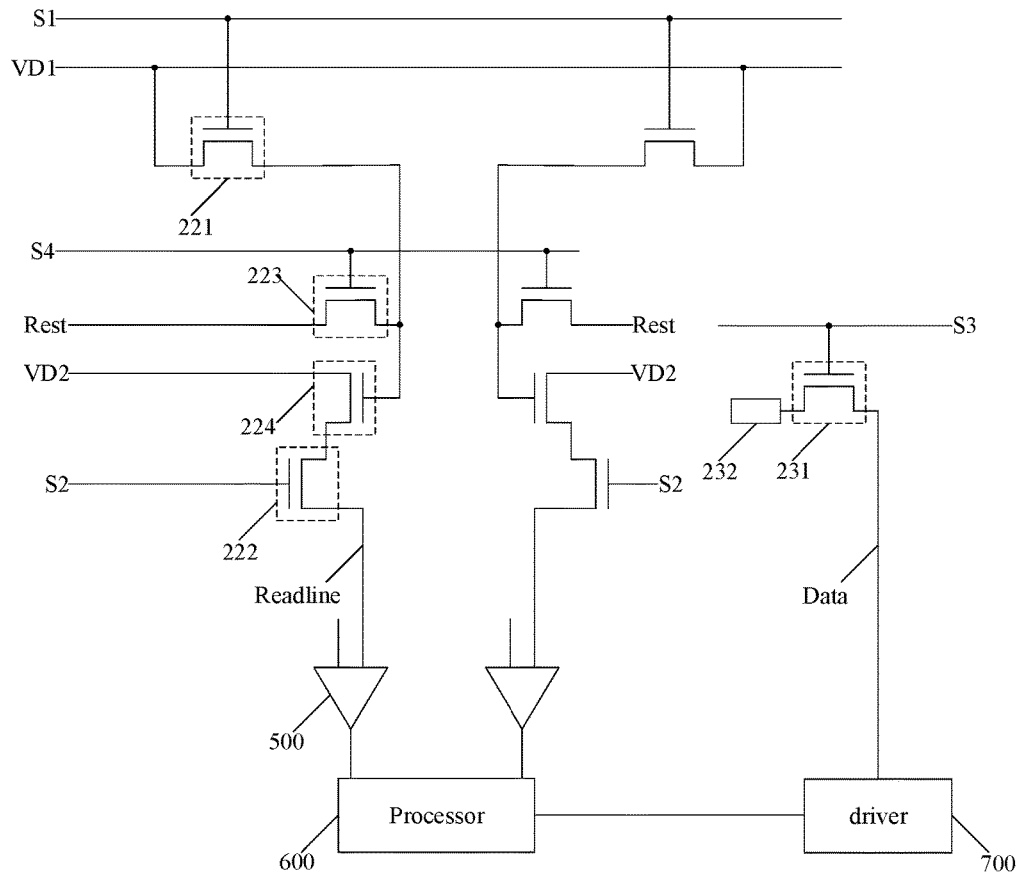
FIG. 3a is a second schematic diagram of a circuit of the microfluidic system according to an embodiment of the present disclosure.

Optionally, in the above microfluidic system, as shown in FIG. 3a, the photosensitivity detection circuit 220 may further include a reset transistor 223 and a follower transistor 224. The reset transistor 223 and the follower transistor 224 are between the photosensitive transistor 221 and the first gating transistor 222.

A gate electrode of the reset transistor 223 is coupled to a fourth scan signal line S4. A source electrode of the reset transistor 223 is coupled to a reset signal line Rest. A drain electrode of the reset transistor 223 is coupled to the drain electrode of the photosensitive transistor 221 and a gate electrode of the follower transistor 224, respectively.

A source electrode of the follower transistor 224 is coupled to a second power supply voltage signal line VD2. A drain electrode of the follower transistor 224 is coupled to the source electrode of the first gating transistor 222.

Figure 3B:
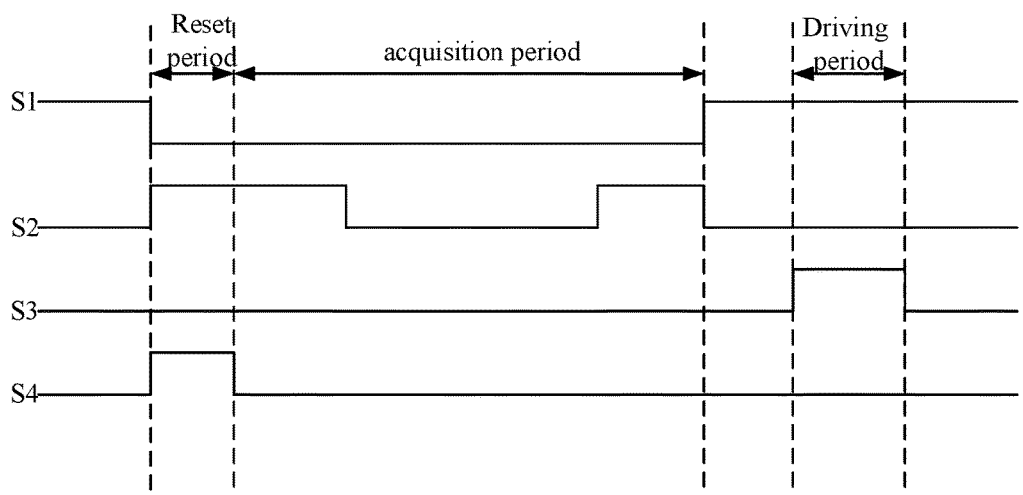

Specifically, as shown in FIG. 3b, in a reset period before the acquisition period, the reset transistor 223 can reset a voltage of the drain electrode of the photosensitive transistor 221 under control of the fourth scan signal line S4. The follower transistor 224 works in a linear region, and can amplify the photocurrent generated by the photosensitive transistor 221 and output the amplified photocurrent. The reset transistor 223, the follower transistor 224 and the first gating transistor 222 together define a light response circuit, which can efficiently reduce the influence of a leakage current of the photosensitive transistor 221 on the photocurrent, thereby improving the signal to noise ratio.

Figure 4A:
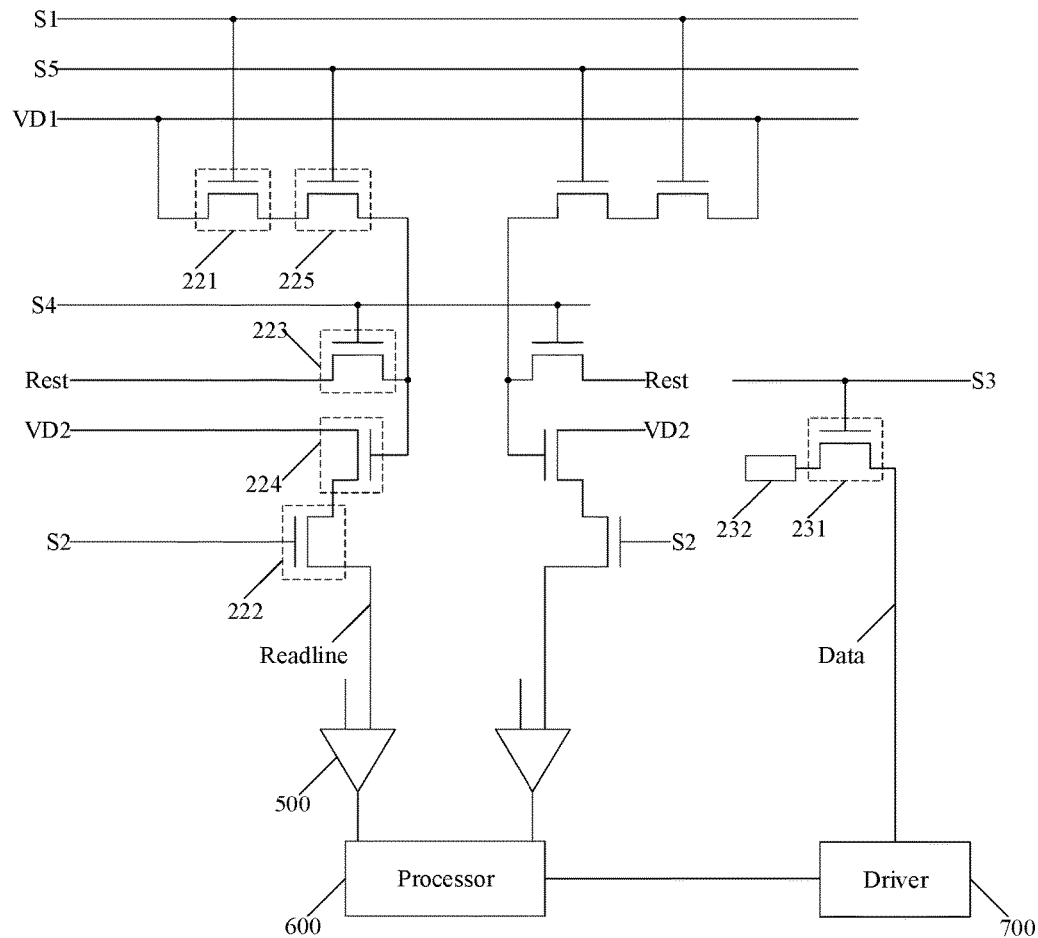
FIG. 4a is a third schematic diagram of a circuit of the microfluidic system according to an embodiment of the present disclosure.

Optionally, in the above microfluidic system, as shown in FIG. 4a, the photosensitivity detection circuit 220 may further include a second gating transistor 225 between the photosensitive transistor 221 and the reset transistor 223. A gate electrode of the second gating transistor 225 is coupled to a fifth scan signal line S5. A source electrode of the second gating transistor 225 is coupled to the drain electrode of the photosensitive transistor 221. A drain electrode of the second gating transistor 225 is coupled to the drain electrode of the reset transistor 223 and the gate electrode of the follower transistor 224.

Figure 4B:
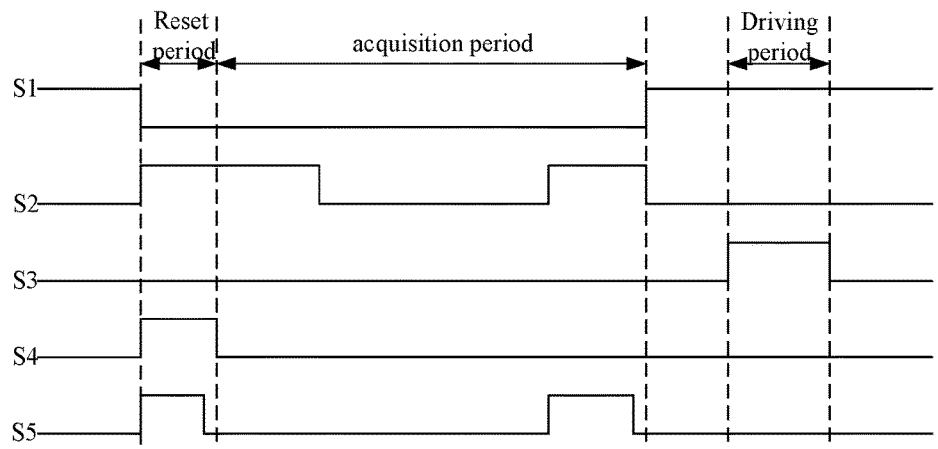
Figure 4C:
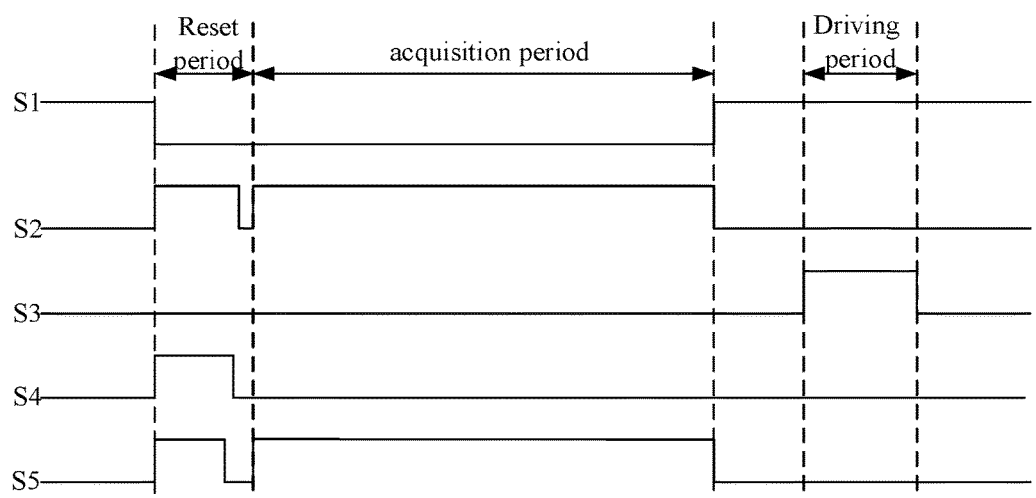

Specifically, as shown in FIG. 4b and FIG. 4c, in a reset period before the acquisition period, the second gating transistor 225 can export the leakage current of the photosensitive transistor 221 under control of the fifth scan signal line S5. In the acquisition period, the second gating transistor 225 can export the photocurrent of the photosensitive transistor 221 under control of the fifth scan signal line S5.

Figure 5A:
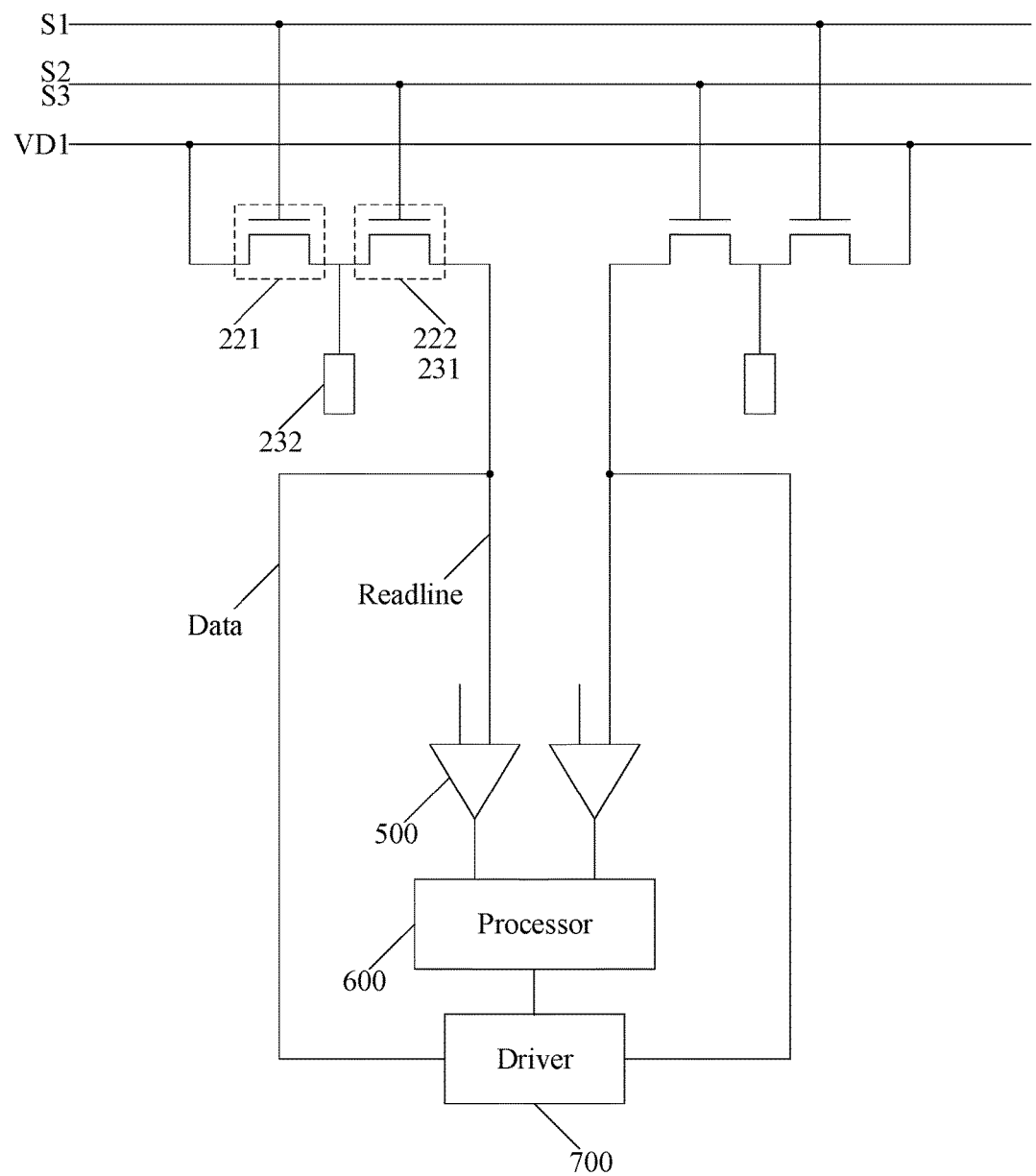
FIG. 5a is a fourth schematic diagram of a circuit of the microfluidic system according to an embodiment of the present disclosure.

Optionally, in the above microfluidic system, as shown in FIG. 5a, the driving transistor 231 and the first gating transistor 222 may be an identical transistor, and the second scan signal line S2 and the third scan signal line S3 may be an identical signal line.

Figure 5B:
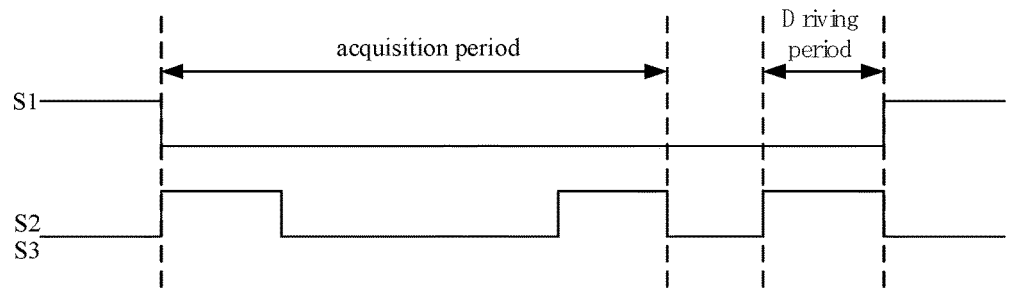

Specifically, when the driving transistor 231 and the first gating transistor 222 are one identical transistor, the number of transistors can be reduced, and the number of devices to be manufactured is also reduced, thereby saving the cost. As shown in FIG. 5b, in an acquisition period, a turn-off signal may be applied to the first scan signal line S1 to enable the photosensitive transistor 221 to be turned off. The photosensitive transistor 221 that is turned off can generate a photocurrent in response to light irradiation. Meanwhile, a turn-on signal may be applied to the second scan signal line S2 to enable the first gating transistor 222 to be turned on. Then, photocurrents generated by the photosensitive transistors 221 can be output through the read signal lines Readline, and a position and a size of the liquid drop can be determined by detecting the signal difference between the photocurrents. Further, in order to avoid influence to acquiring photocurrent signal, the driver 700 is not electrified, i.e., no output.

As shown in FIG. 5b, in a driving period, a voltage of the first power supply voltage signal line VD1 is pulled down, a turn-off signal is applied to the first scan signal line S1 to enable the photosensitive transistor 221 to be turned off, and the integrator 500 is not electrified, i.e., no output. The driver 700 outputs a driving signal, a turn-on signal is applied to the second scan line S2 to enable the first gating transistor 222 to be turned on. Then, the driving signal from the driver 700 is transmitted to the driving electrode 232 through the first gating transistor 222, and drives the liquid drop to move.

Figure 6:
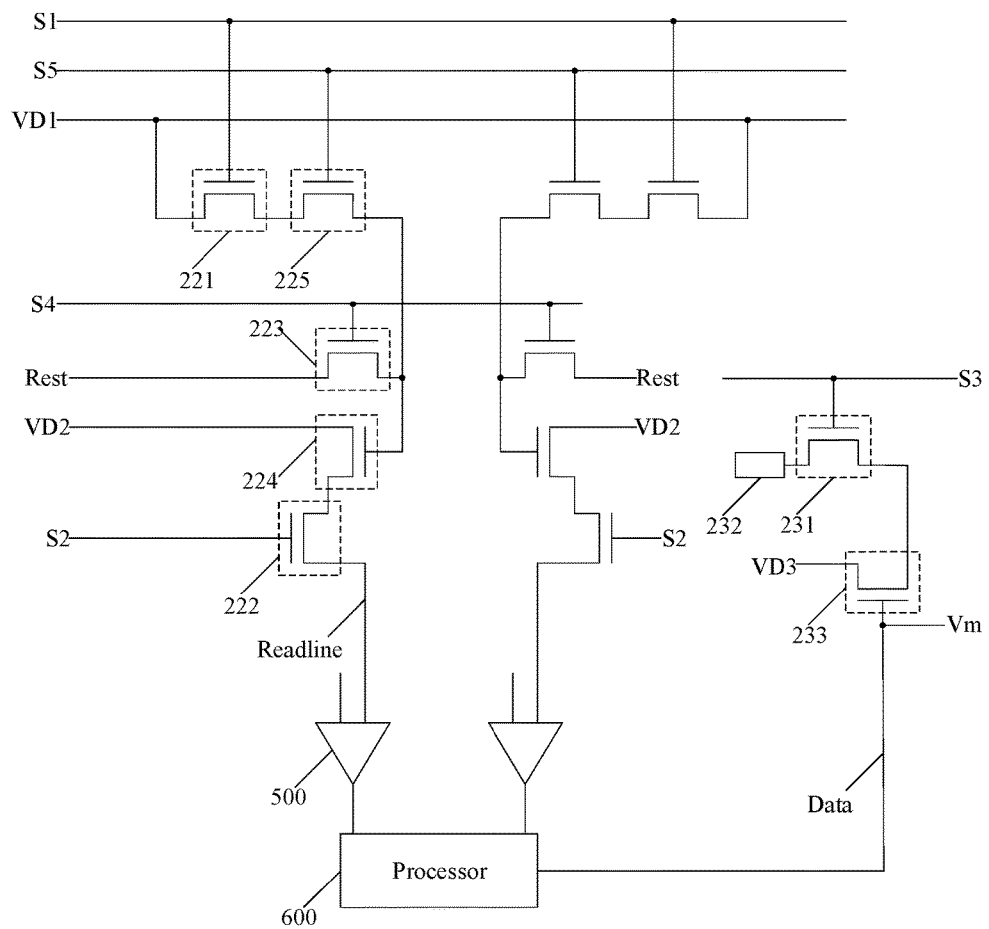
FIG. 6 is a fifth schematic diagram of a circuit of the microfluidic system according to an embodiment of the present disclosure.

Optionally, in the above microfluidic system, as shown in FIG. 6, the driving circuit may further include an amplifier transistor 233 between the driving transistor 231 and the data signal line Data.

A gate electrode of the amplifier transistor 233 is coupled to the data signal line Data and a constant voltage signal line Vm, respectively. A source electrode of the amplifier transistor 233 is coupled to a third power supply voltage signal line VD3. A drain electrode of the amplifier transistor 233 is coupled to the source electrode of the driving transistor 231.

Specifically, an output signal of the amplifier transistor 233 is controlled by a voltage of the constant voltage signal line Vm, thereby enabling the amplifier transistor 233 to work in an amplified state and enabling the amplifier transistor 233 to amplify an output signal of the processor 600 to improve the driving ability. At this point, the driver 700 can be omitted to simplify the system and improve system integration.

Based on the same inventive concept, one embodiment of the present disclosure further provides a method for driving the above microfluidic system. The principle of the method is similar to that of the above microfluidic system, thus implementation of the method may refer to implementation of the microfluidic system, which is repeated herein.

Specifically, as shown in FIG. 2b, the method for driving the above microfluidic system according to one embodiment of the present disclosure includes: in an acquisition period, applying a turn-off signal to the first scan signal line S1, applying a turn-on signal to the second scan signal line S2, and acquiring a signal output from the read signal line Readline; and in a driving period, applying a turn-on signal to the third scan signal line S3, and applying a driving signal to the data signal line Data.

Specifically, in the acquisition period, a turn-off signal may be applied to the first scan signal line S1 to enable the photosensitive transistor 221 to be turned off. The photosensitive transistor 221 that is turned off can generate a photocurrent in response to light irradiation. When light passes through one liquid drop and then is irradiated to some photosensitive transistors 221, these photosensitive transistors 221 can generate a photocurrent. There is a signal difference between the photocurrent generated by one photosensitive transistor 221 that is covered by one liquid drop when light passes through the one liquid drop and then is irradiated to the one photosensitive transistor 221 that is covered by one liquid drop, and a photocurrent generated by one photosensitive transistor 221 that is not covered by any liquid drop when light is directly irradiated to the one photosensitive transistor 221 that is not covered by any liquid drop. In the acquisition period, a turn-on signal may be simultaneously applied to the second scan signal line S2 to enable the first gating transistor 222 to be turned on. Then, photocurrents generated by the photosensitive transistors 221 can be output through the read signal lines Readline, and a position and a size of the liquid drop can be determined by detecting the signal difference between the photocurrents. Then, it is determined which driving circuit 230 is to be controlled by comparing the determined position and size of the liquid drop with a movement trajectory set for the liquid drop. For the driving circuit 230 to be controlled, in the driving period, a turn-on signal is applied to the third scan signal line S3 to enable the driving transistor 231 to transmit a driving signal from the data signal line Data to the driving electrode 230. At this point, a potential difference generated between the driving electrode 230 and the common electrode 400 affects shrink angle of the liquid drop, thereby changing surface tension of the liquid drop and then enabling the liquid drop to move. As a result, the movement trajectory of the liquid drop can be controlled.

Optionally, in the above method, as shown in FIG. 3a, when the photosensitivity detection circuit 220 includes a reset transistor 223 and a follower transistor 224, before the acquisition period, as shown in FIG. 3b, the method may further include: in a reset period, applying a turn-off signal to the first scan signal line S1, applying a turn-on signal to the fourth scan signal line S4, and applying a turn-on signal to the second scan signal line S2.

Specifically, in the reset period, the reset transistor 223 can reset a voltage of the drain electrode of the photosensitive transistor 221 under control of the fourth scan signal line S4, and the reset transistor 223 can export the leakage current of the photosensitive transistor 221 under control of the second scan signal line S2.

Optionally, in the above method, when the photosensitivity detection circuit 220 includes the second gating transistor 225, as shown in FIG. 4a and FIG. 4b, the method may further include: applying a turn-on signal to the fifth scan signal line S4 in the reset period and in the acquisition period.

Specifically, in the reset period, the second gating transistor 225 exports the leakage current of the photosensitive transistor 221 under control of the fifth scan signal line S5; and in the acquisition period, the second gating transistor 225 exports the photocurrent of the photosensitive transistor 221 under control of the fifth scan signal line S5.

Optionally, in the above method, as shown in FIG. 4b and FIG. 4c, in the reset period, a duration for applying the turn-on signal to the fifth scan signal line S5 is less than a duration for applying the turn-on signal to each of the fourth scan signal line S4 and the second scan signal line S2, to better realize the reset effect.

Further, in the acquisition period, a duration for applying the turn-on signal to the fifth scan signal line S5 is less than a duration for applying the turn-on signal to the second scan signal line S2, to leave time for circuits to read signals subsequently.

Optionally, in the above method, as shown in FIG. 4c, in the acquisition period, a turn-on signal can be continuously applied to the second scan signal line S2, to enable the integrator 500 to integrate the photocurrent; or, as shown in FIG. 4b, two turn-on signals with a preset time interval may be applied to the second scan signal line S2, to enable the integrator 500 to integrate photoelectric charges that are obtained through photoelectric conversion and stored in capacitance of the photosensitive transistor 221.

Optionally, in the above method, when the driving transistor 231 and the first gating transistor 222 are one identical transistor, as shown in FIG. 5b, the above method further includes: in the driving period, applying a turn-off signal to the first scan signal line S1, thereby enabling the photosensitive transistor 221 to be turned off and thus avoiding influence to the driving signal of the driving electrode 232.

In the above microfluidic system and the method for driving the same, based on the photosensitive characteristics of the photosensitive transistor, a position and a size of one liquid drop can be detected by using several photosensitivity detection circuits each including the photosensitive transistor and the first gating transistor. In the acquisition period, a turn-off signal may be applied to the first scan signal line to enable the photosensitive transistor to be turned off. The photosensitive transistor that is turned off can generate a photocurrent in response to light irradiation. There is a certain signal difference between the photocurrent generated by one photosensitive transistor when light passes through one liquid drop and then is irradiated to the one photosensitive transistor, and a photocurrent generated by one photosensitive transistor when light is directly irradiated to the one photosensitive transistor. Meanwhile, a turn-on signal may be applied to the second scan signal line to enable the first gating transistor to be turned on. Then, photocurrents generated by the photosensitive transistors can be output through the read signal lines, and a position and a size of the liquid drop can be determined by detecting the signal difference between the photocurrents.

Since the above detection is carried out based on the photosensitive characteristics of the photosensitive transistors, signal interference can be avoided, thereby improving detection accuracy. Then, in the driving period, a turn-on signal is applied to the third scan signal to enable the driving transistor to transmit a driving signal from the data signal line to the driving electrode. A voltage is generated between the driving electrode and the common electrode to control a movement trajectory of the liquid drop. Since both of the photosensitivity detection circuit and the driving circuit implement their functions through transistors without additional detection components, the manufacturing process is simplified and then the manufacturing efficiency can be improved.

The above are merely the optionally embodiments of the present disclosure and shall not be used to limit the scope of the present disclosure. It should be noted that, a person skilled in the art may make improvements and modifications without departing from the principle of the present disclosure, and these improvements and modifications shall also fall within the scope of the present disclosure.

What is claimed is:

1. A microfluidic system comprising:
   an upper substrate;
   a lower substrate that is opposite to the upper substrate;
   a liquid drop accommodation space between the upper substrate and the lower substrate;
   a first hydrophobic layer at an outermost surface of the upper substrate, and the outermost surface of the upper substrate facing the liquid drop accommodation space;
   a second hydrophobic layer at an outermost surface of the lower substrate, and the outermost surface of the lower substrate facing the liquid drop accommodation space;
   a common electrode layer between the upper substrate and the lower substrate;
   an array of photosensitivity detection circuits between the lower substrate and the second hydrophobic layer; and
   an array of driving circuits between the lower substrate and the second hydrophobic layer;
   wherein each photosensitivity detection circuit includes a photosensitive transistor and a first gating transistor;
   wherein a gate electrode of the photosensitive transistor is coupled to a first scan signal line, a source electrode of the photosensitive transistor is coupled to a first power supply voltage signal line, and a drain electrode of the photosensitive transistor is coupled to a source electrode of the first gating transistor;
   wherein a gate electrode of the first gating transistor is coupled to a second scan signal line, and a drain electrode of the first gating transistor is coupled to a read signal line; and
   wherein each driving circuit includes a driving transistor and a driving electrode; a gate electrode of the driving transistor is coupled to a third scan signal line, a source electrode of the driving transistor is coupled to a data signal line, and a drain electrode of the driving transistor is coupled to the driving electrode.

2. The microfluidic system of claim 1, wherein each photosensitivity detection circuit further includes a reset transistor and a follower transistor; and the reset transistor and the follower transistor are between the photosensitive transistor and the first gating transistor;
   wherein a gate electrode of the reset transistor is coupled to a fourth scan signal line; a source electrode of the reset transistor is coupled to a reset signal line; a drain electrode of the reset transistor is coupled to the drain electrode of the photosensitive transistor and a gate electrode of the follower transistor, respectively; and
   wherein a source electrode of the follower transistor is coupled to a second power supply voltage signal line; a drain electrode of the follower transistor is coupled to the source electrode of the first gating transistor.

3. The microfluidic system of claim 2, wherein each photosensitivity detection circuit further includes a second gating transistor between the photosensitive transistor and the reset transistor; and
   wherein a gate electrode of the second gating transistor is coupled to a fifth scan signal line; a source electrode of the second gating transistor is coupled to the drain electrode of the photosensitive transistor; and a drain electrode of the second gating transistor is coupled to the drain electrode of the reset transistor and the gate electrode of the follower transistor.

4. The microfluidic system of claim 1, wherein the driving transistor and the first gating transistor are an identical transistor, and the second scan signal line and the third scan signal line are an identical signal line.

5. The microfluidic system of claim 1, wherein each driving circuit further includes an amplifier transistor between the driving transistor and the data signal line; and
   wherein a gate electrode of the amplifier transistor is coupled to the data signal line and a constant voltage signal line, respectively; a source electrode of the amplifier transistor is coupled to a third power supply voltage signal line; and a drain electrode of the amplifier transistor is coupled to the source electrode of the driving transistor.

6. The microfluidic system of claim 1, further comprising a light shielding layer between the second hydrophobic layer and the photosensitivity detection circuits;
   wherein light transmission structures are formed in the light shielding layer at regions corresponding to some of the photosensitive transistors of the photosensitivity detection circuits.

7. The microfluidic system of claim 6, wherein each light transmission structure is formed in the light shielding layer only at a region corresponding to one of every two adjacent photosensitive transistors.

8. The microfluidic system of claim 7, wherein all transistors of the photosensitivity detection circuits and the driving circuits are bottom gate type transistors in an identical layer.

9. The microfluidic system of claim 1, further comprising a light shielding layer between the second hydrophobic layer and the photosensitivity detection circuits; and wherein the light shielding layer only covers two first gating transistors and one photosensitive transistor of every two adjacent photosensitivity detection circuits.

10. The microfluidic system of claim 1, wherein the common electrode layer is between the upper substrate and the first hydrophobic layer.

11. The microfluidic system of claim 1, further comprising:

a plurality of integrators coupled to read signal lines in a one-to-one manner;
a processor coupled with the integrators; and
a driver coupled with the processor;
wherein the driver is coupled with the data signal lines.

12. A method for driving the microfluidic system of claim 1, comprising:

in an acquisition period, applying a turn-off signal to the first scan signal line, applying a turn-on signal to the second scan signal line, and acquiring a signal output from the read signal line; and
in a driving period, applying a turn-on signal to the third scan signal line, and applying a driving signal to the data signal line.

13. The method of claim 12, wherein each photosensitivity detection circuit includes a reset transistor and a follower transistor, before the acquisition period, the method further includes:

in a reset period, applying a turn-off signal to the first scan signal line, applying a turn-on signal to the fourth scan signal line, and applying a turn-on signal to the second scan signal line.

14. The method of claim 13, wherein each photosensitivity detection circuit further includes a second gating transistor, the method further includes:

applying a turn-on signal to the fifth scan signal line in the reset period and in the acquisition period.

15. The method of claim 14, wherein in the reset period, a duration for applying the turn-on signal to the fifth scan signal line is less than a duration for applying the turn-on signal to each of the fourth scan signal line and the second scan signal line; and wherein in the acquisition period, a duration for applying the turn-on signal to the fifth scan signal line is less than a duration for applying the turn-on signal to the second scan signal line.

16. The method of claim 12, wherein in the acquisition period, the turn-on signal is continuously applied to the second scan signal line.

17. The method of claim 12, wherein in the acquisition period, two turn-on signals with a time interval are applied to the second scan signal line.

18. A microfluidic system comprising:

an upper substrate;
a lower substrate that is opposite to the upper substrate;
a liquid drop accommodation space between the upper substrate and the lower substrate;
a first hydrophobic layer at an outermost surface of the upper substrate, and the outermost surface of the upper substrate facing the liquid drop accommodation space;
a second hydrophobic layer at an outermost surface of the lower substrate, and the outermost surface of the lower substrate facing the liquid drop accommodation space;
a common electrode layer between the upper substrate and the lower substrate;
an array of first photosensitivity detection circuits between the lower substrate and the second hydrophobic layer;
an array of second photosensitivity detection circuits between the lower substrate and the second hydrophobic layer; and
an array of driving circuits between the lower substrate and the second hydrophobic layer;
wherein each of the first photosensitivity detection circuits and second photosensitivity detection circuits includes a photosensitive transistor and a first gating transistor;
wherein a gate electrode of the photosensitive transistor is coupled to a first scan signal line, a source electrode of the photosensitive transistor is coupled to a first power supply voltage signal line, and a drain electrode of the photosensitive transistor is coupled to a source electrode of the first gating transistor;
wherein a gate electrode of the first gating transistor is coupled to a second scan signal line, and a drain electrode of the first gating transistor is coupled to a read signal line;
wherein each driving circuit includes a driving transistor and a driving electrode; a gate electrode of the driving transistor is coupled to a third scan signal line, a source electrode of the driving transistor is coupled to a data signal line, and a drain electrode of the driving transistor is coupled to the driving electrode; and
wherein the photosensitive transistor of each of the first photosensitivity detection circuits is configured to perform optical detection; and the photosensitive transistor of each of the second photosensitivity detection circuits is configured to be used as a comparison transistor.

19. The microfluidic system of claim 18, wherein the first photosensitivity detection circuits and the second photosensitivity detection circuits are alternately arranged.

20. The microfluidic system of claim 19, further comprising a light shielding layer between the second hydrophobic layer and the first and second photosensitivity detection circuits; and wherein the light shielding layer only covers the second photosensitivity detection circuits.

* * * * *